United States Patent
Beard et al.

(10) Patent No.: US 9,109,999 B2
(45) Date of Patent: Aug. 18, 2015

(54) TRANSDUCER ARRAY SELF-DIAGNOSTICS AND SELF-HEALING

(75) Inventors: Shawn J. Beard, Livermore, CA (US); Chang Zhang, Santa Clara, CA (US); Xinlin Qing, Cupertino, CA (US)

(73) Assignee: ACELLENT TECHNOLOGIES, INC., Sunnyvale, CA (US)

( * ) Notice: Subject to any disclaimer, the term of this patent is extended or adjusted under 35 U.S.C. 154(b) by 433 days.

(21) Appl. No.: 12/039,600

(22) Filed: Feb. 28, 2008

(65) Prior Publication Data
US 2008/0255781 A1 Oct. 16, 2008

Related U.S. Application Data

(60) Provisional application No. 60/912,112, filed on Apr. 16, 2007.

(51) Int. Cl.
| | |
|---|---|
| *G06F 11/30* | (2006.01) |
| *G01C 25/00* | (2006.01) |
| *G01R 15/00* | (2006.01) |
| *G01R 31/00* | (2006.01) |
| *G01N 29/00* | (2006.01) |
| *G01D 7/00* | (2006.01) |
| *G01N 29/04* | (2006.01) |
| *G01N 29/36* | (2006.01) |
| *G01N 29/44* | (2006.01) |

(52) U.S. Cl.
CPC .............. *G01N 29/041* (2013.01); *G01N 29/36* (2013.01); *G01N 29/4463* (2013.01); *G01N 2291/0427* (2013.01); *G01N 2291/106* (2013.01)

(58) Field of Classification Search
CPC .......................... G01N 29/041; G01N 29/4463
USPC ............ 702/34, 35, 57–59, 64, 65, 104, 116, 702/117, 118, 124, 126, 183, 185, 189, 193, 702/198; 73/1.82, 862.046, 587, 767, 602, 73/768; 324/691, 525, 527, 522, 523, 681, 324/637
See application file for complete search history.

(56) References Cited

U.S. PATENT DOCUMENTS

| | | | | |
|---|---|---|---|---|
| 5,345,182 | A | * | 9/1994 | Wakamatsu ................... 324/649 |
| 6,006,163 | A | * | 12/1999 | Lichtenwalner et al. ........ 702/36 |
| 7,366,627 | B2 | * | 4/2008 | Gordon et al. ................. 702/105 |

(Continued)

OTHER PUBLICATIONS

P.M. Flanagan et al.; Developing a Self-Diagnostic System for Piezoelectric Sensors; 1990; pp. 1-5, AIAA/SAE/ASME/ASEE 26th Joint Propulsion Conference, Orlando, FL.*

(Continued)

*Primary Examiner* — Sujoy Kundu
*Assistant Examiner* — Ricky Ngon
(74) *Attorney, Agent, or Firm* — Innovation Counsel LLP

(57) ABSTRACT

A method of performing transducer self-diagnostics and self-healing on an array of sensor transducers bonded to a structure for health monitoring includes measuring impedance to detect whether a transducer is missing, or a connection is damaged. Pitch-catch signals generated between one or more pairs of transducers are analyzed for detecting defects according to selected criteria of defect size and location to determine whether the sensors are damaged or partially/fully disbonded. Based on the resulting map of operational transducers, signal transmission paths are added/extended between additional pairs of transducers to maintain inspection coverage of the structure according to the selected criteria.

6 Claims, 8 Drawing Sheets

(56) References Cited

U.S. PATENT DOCUMENTS

| | | | |
|---|---|---|---|
| 7,487,059 B2 * | 2/2009 | Davis et al. | 702/116 |
| 7,627,439 B1 * | 12/2009 | Kessler et al. | 702/35 |
| 2005/0068041 A1 * | 3/2005 | Kress et al. | 324/527 |

OTHER PUBLICATIONS

Timothy G.S. Overly et al.; Development of Signal Processing Tools and Hardware for Piezoelectric Sensor Diagnostic Processes.*

Gyu Hae Park et al.; Performance assessment and validation of piezoelectric active-sensors in structural health monitoring, 2006; pp. 1673-1683, vol. 15, Smart. Mater Struct., IOP Publishing LTd.*

Castanien et al., "Application of active structural health monitoring technique to aircraft fuselage structures", 1996, Proceedings, SPIE Symposium on Smart Structures and Materials, vol. 2721, pp. 38-49.*

Peairs et al., "Low Cost Impedance Monitoring Using Smart Materials", 2002, Proceeding of the First European Workshop on Structural Health Monitoring, Ecole Normale Superieure, Cachan (Paris), France. pp. 1-9.*

Gyu Hae Park et al.; Performance assessment and validation of piezoelectric active-sensors in structural health monitoring, 2006; pp. 1673-1683. vol. 15, Smart. Mater Struct., IOP Publishing LTd.*

Timothy G.S. Overly et al.; Development of Signal Processing Tools and Hardware for Piezoelectric Sensor Diagnostic Processes. 2007.*

Giurgiutiu et al., "Active Sensors for Health Monitoring of Aging Aerospace Structures", 2000, SPIE, vol. 3985, pp. 294-305.*

* cited by examiner

TRANSDUCER ARRAY SELF-DIAGNOSTICS AND SELF-HEALING

This application claims the benefit of U.S. Provisional Patent Application Ser. No. 60/912,112, entitled "STRUCTURAL HEALTH MONITORING SYSTEM AND METHODS FOR USE," filed on Apr. 16, 2007, which is hereby incorporated by reference in its entirety.

This invention was made with Government support under contract number W31P4Q-05-CR064 awarded by the U.S. Army. The Government has certain rights in the invention.

TECHNICAL FIELD

This invention relates generally to structural health monitoring. More specifically, this invention relates to performing comprehensive self-diagnostics of the structural health monitoring transducers themselves.

BACKGROUND

A transducer array may be attached to or embedded within a structure for diagnosis of the integrity (i.e., health) of the structure. Crack defects above a certain size may compromise the health of the structure. The transducer, which may be a passive sensor for detecting, an active transducer for exciting signals that propagate through the structure when an electrical signal is applied, or both, may sense and/or excite signals in the structure to detect cracks, and the transducers may be controlled by electronics associated with the transducer array.

Current active damage detection techniques have been shown to be highly accurate and reliable for detecting structural damage when all of the transducers are healthy and functional. However, if one or more transducers are degraded, damaged, or missing, the structural health monitoring system may not function properly and give false indications of structural damage which, in reality, is a health monitoring system failure.

To make the diagnostic function of a structural health monitoring system more robust in the presence of degraded, damaged, or missing transducers, there is a need for transducer and system self-diagnostics to include the ability to accurately detect and identify which transducers are degraded, damaged, or missing. Additionally, there is a need for a built-in capacity for self-healing or self-compensation to maintain a satisfactory level of health monitoring performance.

SUMMARY

According to one embodiment of the present disclosure, a method of performing self-diagnostics on an array of transducers includes measuring transducer impedance to detect whether a transducer is missing, or a connection is damaged. Pitch-catch signals are generated between one or more pairs of transducers. The obtained pitch-catch signals are analyzed according to selected criteria to determine whether the sensors are damaged or partially or fully disbanded.

In an embodiment of the disclosure, a method of transducer array fault diagnostics includes defining location coordinates for one or more of the transducers of the array. An identifier number is assigned to each transducer. A corresponding electrical connection channel identifier is associated with each transducer. A data input file is assembled, wherein the file comprises the transducer identifier and the channel identifier and, optionally, the transducer location coordinates. An impedance diagnostic measurement process is performed, wherein an impedance measurement is made in association with each of the one or more transducers measured. A fault code is assigned to each of the one or more transducers on the basis of the impedance diagnostic measurement process. An impedance diagnostic output file is created, wherein the output file comprises the fault code associated with each of the one or more transducers. The impedance diagnostic output file is stored in a memory, and the status of the one or more transducers is reported on the basis of the diagnostic output file.

In an embodiment of the present disclosure, a method of impedance measuring includes applying a waveform voltage to at least one sensor transducer to measure the impedance. The measured impedance is compared to a reference value of impedance corresponding to a satisfactory transducer. Based on the impedance measurement a determination is made whether the transducer indicates an open, short or normal circuit connection.

In an embodiment of the disclosure, a method for self-healing an array of transducers includes identifying faulty transducers in the array and determining the remaining operational transducers. A net of possible usable paths is generated for signal transmission between the remaining operational transducers, and paths associated with faulty transducers are removed from the net. The remaining paths are analyzed to determine whether these paths are sufficient to provide coverage of a region encompassed by the array to detect defects of a selected minimum size or larger. Pitch-catch signal transmission is performed between pairs of operational transducers to determine if any transducers, while electrically operational, are disbanded. Where disbonds are detected, signal transmission paths between are added or extended to neighboring transducers to provide sufficient coverage.

In an embodiment of the disclosure, a system for transducer array self-diagnostics includes an array of transducers, an impedance measurement system to characterize the electrical impedance of the transducers, a signal generation and detection system to transmit signals between pairs of transducers, and a controlling computer running one or more programs stored on a computer readable medium adapted to control the impedance measurement system, the signal transmission system and analyze the impedance and transmission information to self-diagnose and heal the health monitoring capability of the array.

These and other features and advantages of the present invention will be more readily apparent from the detailed description of the preferred embodiments set forth below taken in conjunction with the accompanying drawings.

BRIEF DESCRIPTION OF THE FIGURES

Like element numbers in different figures represent the same or similar elements.

DETAILED DESCRIPTION

Transducer arrays for diagnostic monitoring of the health of structures are described in U.S. Pat. No. 6,370,964 to Chang, et al., and U.S. Pat. Pub. No. 2007/0018083, both of which are hereby incorporated by reference in their entirety. Typically, transducers in structural health monitoring systems comprise piezoelectric ceramic or polymer materials, where transduction occurs between electrical signals and elastic deformation of the material. The following discussion is most easily understood by referring to such exemplary transducers, but the disclosure is not intended to be limiting.

Figure 1:
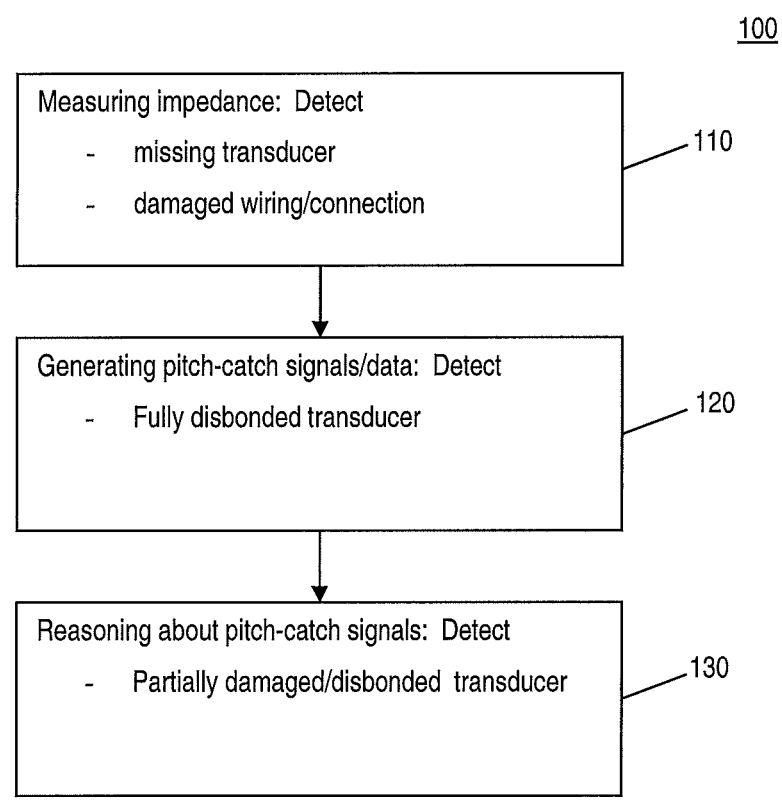
FIG. 1 illustrates a three step method to detect faulty sensor array elements according to an embodiment of the present disclosure.

There are many different reasons that a sensor transducer affixed to a structure for health monitoring may stop functioning, or function sub-optimally. Possible failure modes may include a short or an open circuit, either due to a wiring or transducer fabrication or assembly defect, or a cable malfunction. FIG. 1 illustrates a method 100 including an integrated three-step process that may automatically detect faulty transducer array elements (where transducer may refer to a signal sensor, an actuator, or a dual sensor-actuator) of a structural health monitoring system, wherein the defect may be described at least by a missing transducer, damaged connection/wiring, or a transducer that is still connected to the array, but is damaged or partially or completely disbanded from the structure. Additional defects may occur, and the description here is intended to be exemplary and not limiting. The first step may include measuring impedances (block 110) to detect a missing transducer or damaged connection/wiring. An exemplary system for making the impedance measurement is described below. The second step may include generating and analyzing pitch-catch (e.g., elastic wave) signals (block 120) excited between selected pairs of transducers. The existence/nonexistence of a signal (i.e., whether a signal is detected or not) may be used to identify the presence of a fully disbanded transducer. The third step may include reasoning about pitch-catch signal data (block 130) to identify a partially damaged or disbanded transducer.

Figure 2:
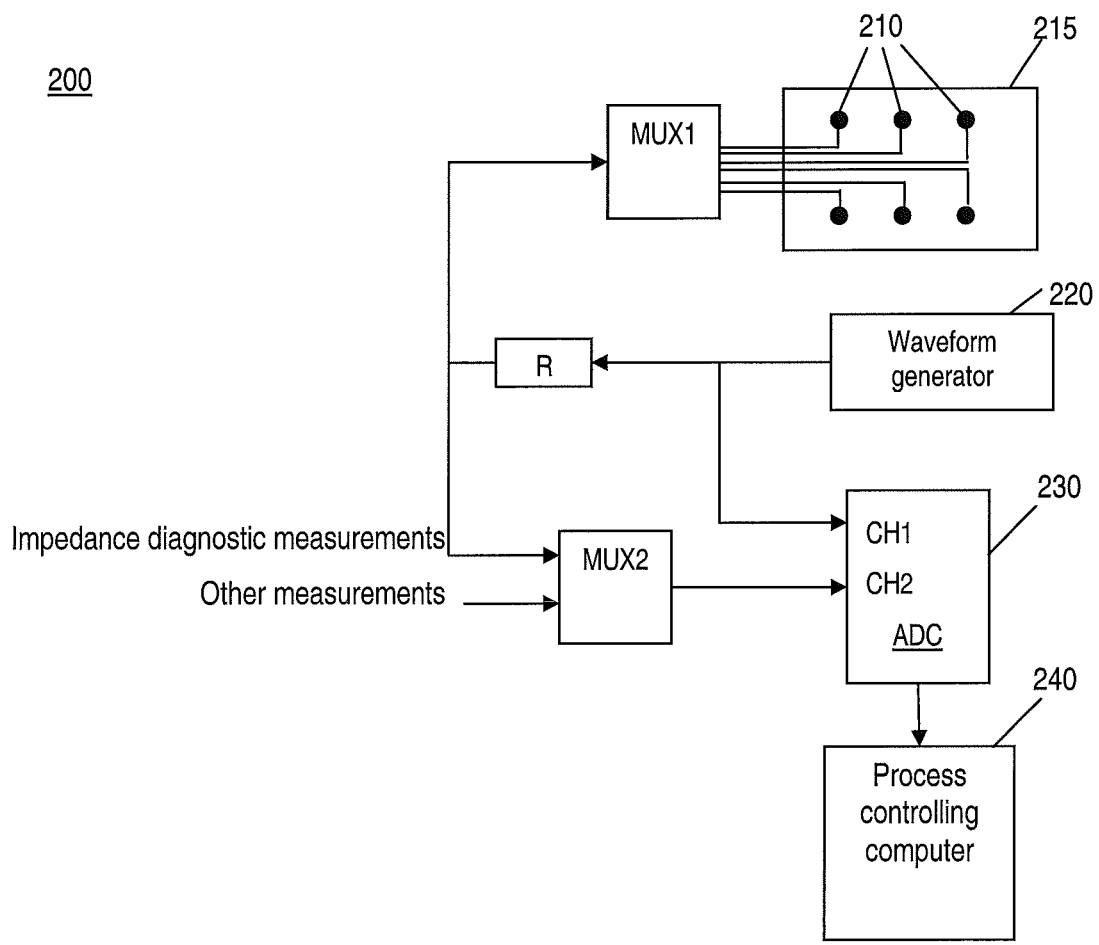
FIG. 2 is a block diagram of a system for an impedance-based method for diagnosing sensor status according to an embodiment of the present disclosure.

Measuring impedance (block 110) of a transducer and detecting wire or cable defects in an array may be accomplished, for example, using an array impedance measurement system 200, as shown in FIG. 2. System 200 may be integrated with an operational structural health monitoring system (not shown). An array 215 of transducers 210 may be configured on a structure (not shown). MUX1 provides multiplex connections to each of transducers 210, which can be addressed individually or multiply by toggling MUX1 connections. MUX2 toggles between normal diagnostic measurement mode ("other measurements") which may include structural health monitoring and/or pitch-catch diagnostics, and impedance self-diagnostic measurement mode. Analog signals are input at two channels CH1 and CH2 of an analog-to-digital (A/D) converter ADC 230. CH1 receives an electrical waveform signal directly from a waveform signal generator 220. Waveform generator 220 provides an electrical signal to excite one or more selected transducers 210 of array 215 through a reference resistor R and MUX1. CH2 receives a voltage signal as measured from the other side of resistor R via MUX2. The two signal voltages measured by CH1 and CH2 thus measure voltage levels on both sides of reference resistor R (and MUX2, as will now be discussed). ADC 230 may then provide the signal information as digital data to a processing computer 240 that executes a program stored in a memory (not shown) to control the impedance measurement process. Additionally, processing computer 240 may be configured to control switching in MUX1 and MUX2, as well as the operation of waveform (signal) generator 220, and ADC 230.

The measuring of impedance parameters takes place substantially as follows: CH1 measures a voltage signal V1 from a waveform generator. CH2 measures a voltage signal from a circuit that includes at least one of the transducers, MUX1, a reference resistor R and a waveform generator 220. Typically, the impedance of ADC 230 at CH1 and CH2 is very high, so as not to draw current or shift voltages being measured to any significant degree, as is well known in the art of electronic measurement.

Figure 3:
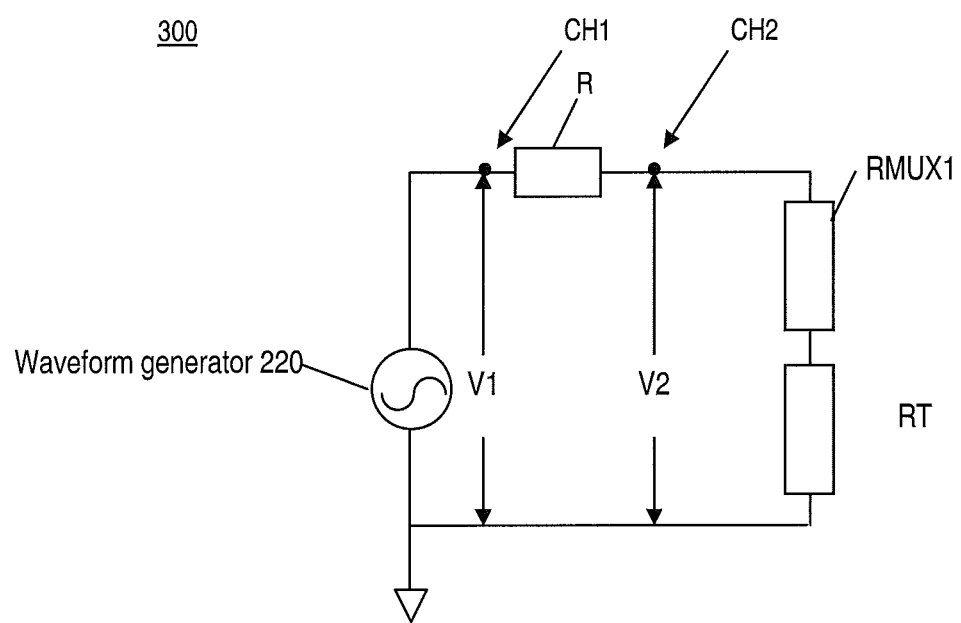
FIG. 3 illustrates an equivalent circuit that may be used to represent the system of FIG. 2.

FIG. 3 is an equivalent circuit 300 that may be used to represent system 200. The impedances of various elements of the system are designated as follows: R is the impedance of the reference resistor, RMUX1 and RMUX2 are impedances of MUX1 and MUX2, and RT is the impedance of an individual transducer 210 at a selected frequency. For reasons discussed above, the presence of RMUX2 may be neglected since its characteristic impedance may typically be nearly negligible as compared to the impedance of CH2 in ADC 230, as a negligible amount of current may flow through it, with a consequent negligible voltage drop relative to other components of system 200, and will thus be ignored to simplify the analysis.

Transducer 210 may be, for example, a PZT (lead zirconate titanate) piezoelectric ceramic transducer, which may be used both as a passive sensor or actuator to excite and detect elastic wave signals. Piezoelectric polymer transducers may also be used, more particularly as passive sensors. The selected frequency may be chosen at the resonance of a bonded transducer 210, where coupling between transducer 210 bonded to the structure is most effective for excitation or detection of elastic waves that propagate across the structure. V1 is the frequency dependent signal generated by waveform generator 220, and is detected at CH1, where it is converted to a digital signal by ADC 230. V2 measures the signal at RMUX2, but that is essentially the same voltage signal resulting between R and RMUX1, according to the assumption stated earlier.

If transducer 210 is excited at a selected frequency, V2 may have a phase relationship relative to V1. For example, at a frequency corresponding to transducer elastic wave excitation resonance, the relative phase may be approximately zero degrees, and the voltage relationship V1/V2 may be substantially pure real (i.e., having a zero relative phase). Assuming that CH1 and CH2 have relatively very large and, therefore effectively infinite impedances, so that negligible current flows through MUX2, the impedance of MUX2 may be neglected, and the effective voltage ratio V2/V1 is given by:

$$\frac{V2}{V1} \approx \frac{RMUX1 + RT}{R + RMUX1 + RT}$$

When a wire connected to transducer 210 is broken, there is an open circuit, i.e., RT is effectively infinite and is thus the dominant term of the above equation, so that V2 is approximately V1. When there is a short in the connection, RT is 0, and V2/V1 has a minimum value, determined by R and RMUX1 alone. At a selected frequency, which may be the excitation resonance frequency of PZT transducer 210, an intermediate value of V2/V1 may be obtained. So by measuring the values of V1 and V2, it may be possible to determine easily and immediately if there is an open circuit, short circuit, a normal or abnormally functioning transducer. A transducer 210 that functions abnormally may be determined by a signal ratio V2/V1 that is intermediate in value, as described above, but outside a selected range of variability that defines a normal transducer. This may happen, for example, when a partial disbond occurs and the electromechanical impedance conditions of transducer 210 are thus altered, as discussed below.

By measuring the amplitude and phase of V2/V1 as a function of frequency, the resonant frequency and quality factor of transducer 210 may be measured. These values may be expected to fall into a certain acceptable range if transducer 210 is normal and properly bonded and the wire connections are properly intact, but the ratio V2/V1 may shift if the integrity of the bond is questionable or the electromechanical property of transducer 210 has changed.

For example, in a large transducer array network 215, if several or all transducers 210 are diagnosed as open circuit, then one may reasonably conclude that the cable wire is damaged. As another example, if the resonance frequency and quality factor differ from what may be expected from a properly bonded transducer (unbonded, or disbanded transducers may, for example, exhibit a higher quality factor and a higher resonance frequency) then information about the quality of the bond may be obtained.

Statistical methods can also be used to detect degradation of transducers 210 when there are a sufficiently large numbers of transducers to establish value norms, and the equivalent circuit properties may then be expected to fall into a limited range of values. Assume that the average normalized value of V2/V1 is <V> for an array 215 of normal, i.e., nominally identical, functional transducers 210 that are properly bonded. A normal transducer 210 may produce a V2/V1 ratio within a given range [<V>−α, <V>+α]. If a given V2/V1 value is outside the range, then transducer 215 may be defective due to connection, material or bonding effects.

Figure 4:
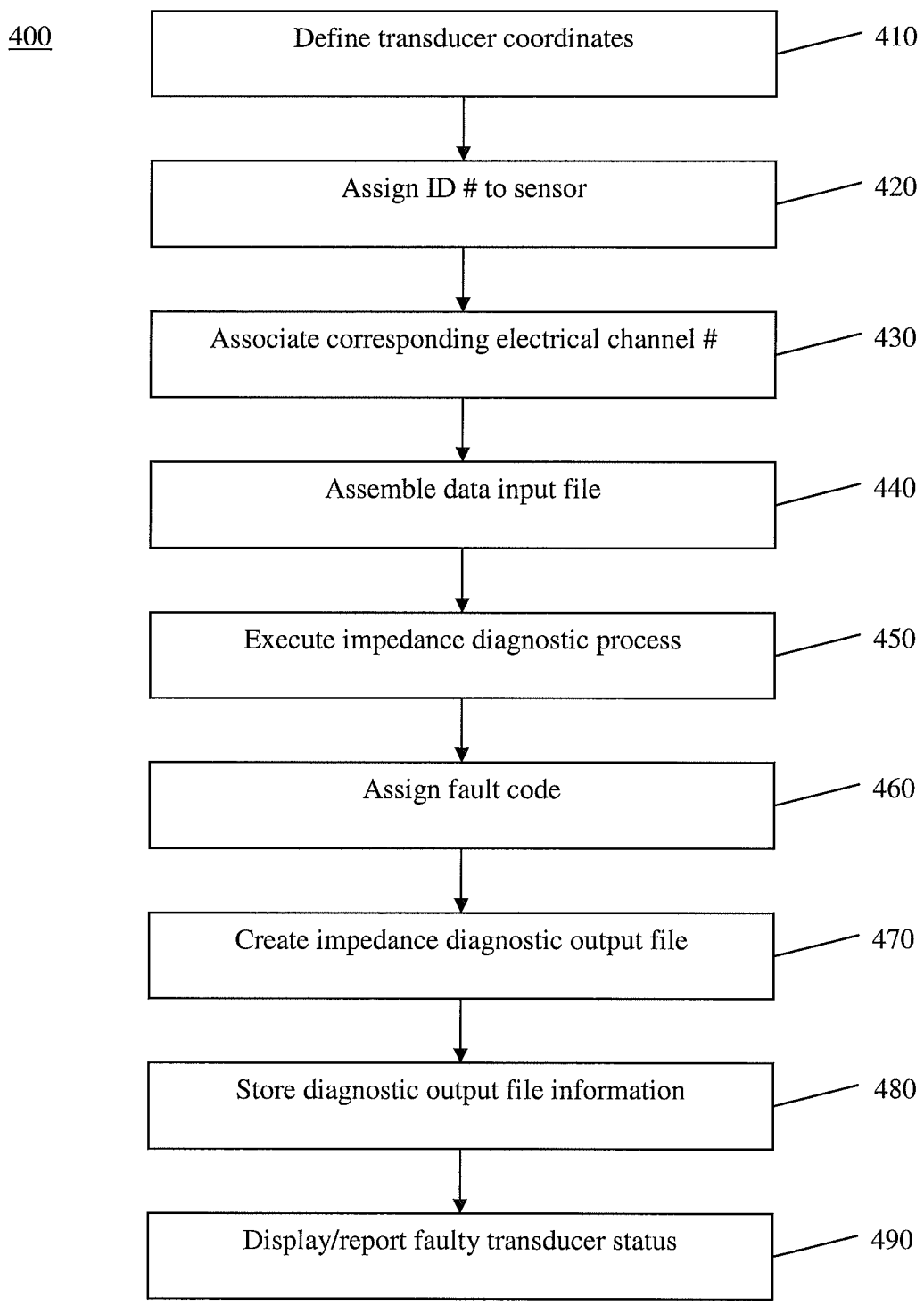
FIG. 4 illustrates a method of diagnosing transducer faults by impedance measurements according to an embodiment of the present disclosure.

FIG. 4 is a block diagram illustrating a method 400 of implementing the impedance measurement of block 110 of FIG. 1. Transducer configuration layout parameters may first be specified. This may include defining transducer coordinate parameters (block 410), assigning a transducer ID number (block 420) to each transducer, and identifying a corresponding electrical channel number for connection to the transducer (block 430). A data input file may be assembled (block 440). Transducer numbering and channel numbering need not be identical sequences, as the data input file can maintain the correspondence between them.

An impedance diagnosis process (block 450) is then executed to read the data input file, and control impedance diagnosis system 100 to measure the impedance of each transducer. The diagnosis process assigns fault codes to each transducer (block 460) based on the impedance measurement, and creates an impedance diagnosis output file (block 470) associating the fault diagnosis with the respective transducer. The impedance diagnosis output file is stored in a computer memory. The contents of the diagnosis output file are then read from memory for displaying in graphical and/or report form (block 490) a diagnostic display and/or report of faulty transducers and associated probable cause according to the fault code.

An exemplary case of a data input file is presented below. A first sequence consists of measurement parameters. For example, the following line may be interpreted as follows:
 10 20000 500000 5000 1000 1 1 2500 4 1 1
 Explanation:
  10 transducers
  20000 Hz start frequency
  50000 Hz end frequency
  5000 Hz step increments
  Remaining parameters may be reserved for future use.

A second sequence of lines may form two or more columns, the first column indicating the transducer number (e.g., 1-10, in this case), and the second column indicating the corresponding channel, as identified, for example, in MUX2. Optionally, two or more additional columns may be included, which provide the x-, y-, and optionally z-coordinate (if applicable) of the corresponding transducers. In the case of an array of transducers affixed to a "sheet" or known flexible layer applied to a structure, only two coordinate dimensions may be needed, relative to the sheet, even if the sheet is applied to a structure surface having curvature.

Impedance diagnosis process 450 then controls impedance measurement system 100, generating instructions based on the contents of the data input file. Impedance diagnosis process (block 450) then assigns fault codes (block 460) and generates an impedance diagnosis output file (block 470). The diagnosis output file may be, for example, an ASCII file comprised of two columns, where the first column may be the sensor number, and the second column may list the associated fault code, as determined by the impedance diagnosis process. For example, the fault code may comprise four values, which may be defined as shown in Table 1:

TABLE 1

| Fault Code | |
|---|---|
| 0: | Normal |
| 1: | PZT sensor open circuit or broken |
| 2: | PZT sensor circuit shortage |
| 3: | Cables: not connected, damaged, or incorrectly connected |

Such fault codes are may generally be considered as pass/fail indicators. Additional fault codes may be conceived as the necessity arises for monitoring structures with different types of transducers or sensors. Display process (block 490) then reads the fault codes and generates a graphical diagnostic display and/or report.

Figure 5:
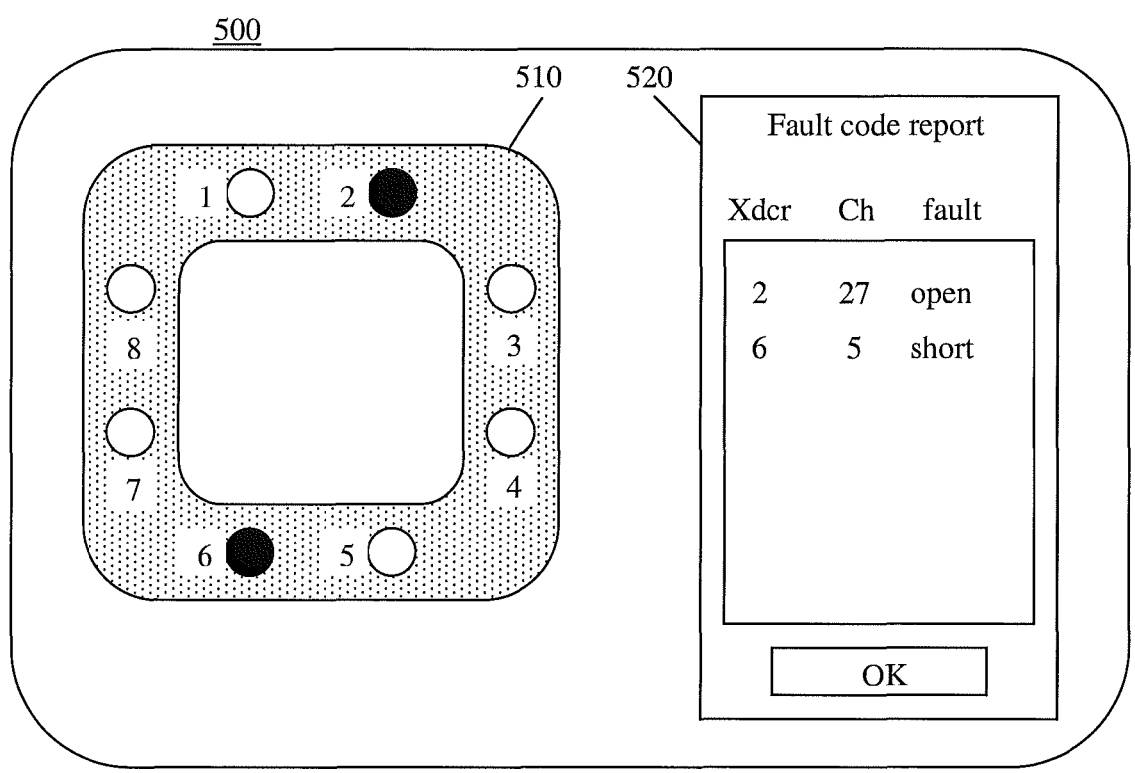
FIG. 5 illustrates a graphical display of a transducer layout and defect report, according to an embodiment of the present disclosure.

FIG. 5 illustrates a graphical display 500 of a transducer layout and defect report, according to an embodiment of the present disclosure. In the example shown, transducers 210 (numbered 1 to 8) are positions on a structure that may be a cutout, such as the frame of an airliner window. In the example, transducers 2 and 6 are identified as faulty, according to impedance diagnosis output file (block 470, FIG. 4). They thus may be indicated graphically as faulty by color coding, on a display of the physical layout 510 indicating the transducer location. Additionally, a displayed report 520 may summarize the list of identified faulty transducers, the corresponding electrical channel and the fault type, e.g., open, short, cable, etc. When transducers are flagged as faulty by the above criteria, all signal data related to these transducers will be subsequently removed from further analysis, as will be discussed below.

Figure 6:
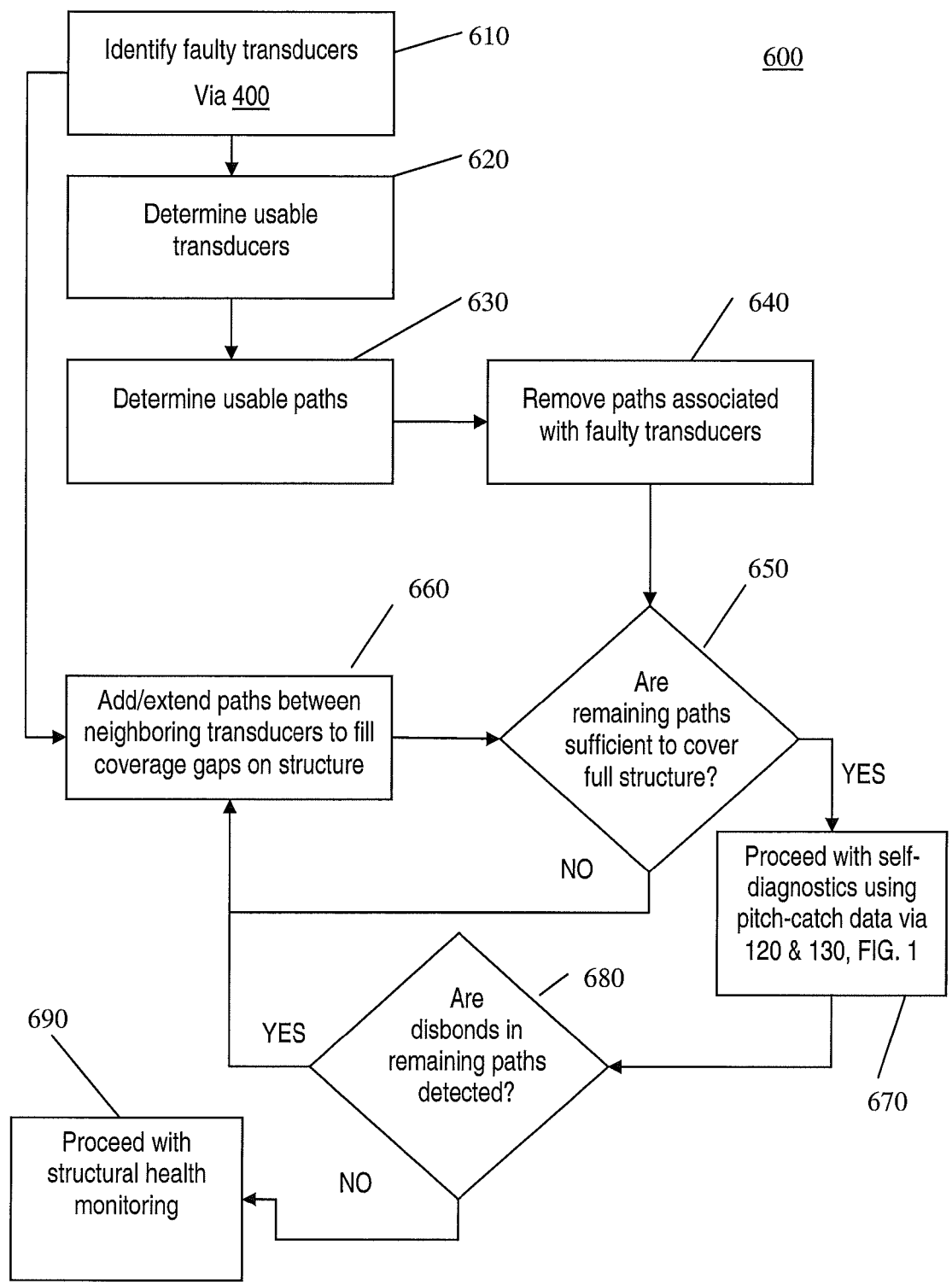
FIG. 6 illustrates a method of self-diagnostics and self-healing in a transducer array, according to an embodiment of the present disclosure.

Measuring the impedance of each transducer 210 may be used to find an open or short circuit. This may indicate that the transducer is missing or there is a damaged wire connection. However, a degraded or damaged transducer may still go undetected using the impedance method due to statistical variability of material, or due to bonding or wire connection properties that may each be only partially defective but still result in an impedance measurement within the ±α margin of test acceptability. To resolve this, a reasoning method 600, illustrated in the flow chart in FIG. 6, includes steps for generating and transmitting pitch-catch signals (in block 120, FIG. 1) between pairs of transducers 210 based on the data in the diagnosis output file (of block 470, FIG. 4), and then applying a reasoning process 600 based on the signals obtained to detect degraded or damaged transducers 210 (e.g., disbonds) that the impedance method may miss.

Faulty transducer identification (block 610), using method 400, determines whether and which transducers 210 may be electrically faulty. A list of remaining transducers is generated (block 620), and the remaining population of transducers 210 is used to generate an initial list of possible usable paths between the remaining transducers (block 630). The initial list may, for example be generated by finding the next shortest paths that would detect a fault or replicate at least the path lost by elimination of a transducer. All paths associated with at least one faulty transducer are removed from the path net (block 640). A reasoning process (block 650) analyzes the specified path net to determine if it provides sufficient coverage of the structure. Determination of sufficiency will be described in more detail below.

If the current path net is not sufficient to cover the structure sufficiently (i.e., a NO result in block 650), additional paths are added or extended through the location of the faulty transducer to provide the equivalent path coverage (block 660). If the resulting path net is determined to provide sufficient coverage for detecting defects of at least a minimum size (in block 650) (i.e., a YES result), then self diagnostics and reasoning about array 215 may proceed by generating pitch-catch signals between the transducers 210 of array 215 that remain (block 670).

If all remaining transducers 210 pass the impedance test measurement (of block 110, FIG. 1) (i.e., there is no open or short circuit), and paths between pairs of transducers 210 using the pitch-catch method result in either no signal or only a weak signal recorded between neighboring sensor transducers for all pitch-catch paths associated with a given transducer 210 (using the method of block 120, FIG. 1), then this may indicate a transducer 210 is electrically intact, but may be completely or partially disbanded from the structure. Such a transducer 210 would therefore be incapable of detecting or exciting an elastic wave signal on the structure, or only weakly capable of doing so. Partial disbanding is one example of degradation.

A more detailed reasoning process may be used to check for degraded transducers. This reasoning process involves comparing signals on paths going directly through a suspect transducer 210 to signals obtained from prior baseline measurements. If there are signal differences between the obtained data and baseline data for all actuator-sensor paths associated with a given PZT transducer, but there are no substantial signal changes on paths going directly through a particular transducer in question to a third transducer directly in line with the first two, then this is an indication of a degraded transducer (for example, partially damaged or disbanded).

Figure 7:
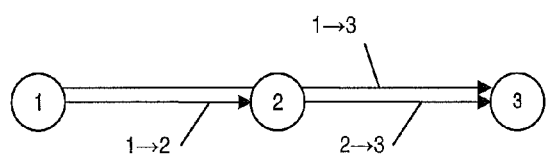
FIG. 7 illustrates another method of determining disbanded transducers in an array, according to an embodiment of the present disclosure.

For example, referring to FIG. 7, assuming that all transducers 210 under consideration satisfy the impedance matching measurement criteria of block 110 as applied in system 200 according to equivalent circuit 300, if paths 1→2 and 2→3 between transducers #1 and #2 and between #2 and #3 show signal changes, including either a weakened signal or loss of signal, but path 1→3 between transducers 1 and 3 does not show any changes relative to baseline data records, then this may indicate transducer #2 may be partially damaged or completely disbanded. Similarly, if path 1→2 shows no change, but 1→3 and 2→3 show changes, then this indicates that transducer #3 is suspected of degradation. Because the configuration is symmetric about transducer #2, #1 may be similarly diagnosed. Alternative combinations, in which the path direction is reversed, may be considered, and reciprocity predicts that the observed results will be the same. Thus, if array 215 has at least three transducers 210 arranged in line with each other, and one of the transducers may be defective, it can be identified, whether it is an interior transducer 210 of array 215 or an edge transducer 210 of array 215.

Given this ability to detect disbanded transducers, which may impact the capacity of an array 215 with a designated set of pitch-catch paths to detect structural defects of a given minimum size, the next step in self-diagnostics involves strategies for "self-healing" array 215 to retain the full coverage of the structure. Self-healing is an adaptive process, for example, of adding new pitch-catch paths between different pairs of transducers than were previously selected in order to cover the same area as previously provided, or to guarantee that the new paths provide coverage that enables detection of defects having greater than a specified minimum size within the array area. FIG. 8 illustrates, as an exemplary case, how new-path generation can be implemented to maintain coverage in a 3×3 array 815 of transducers 810 for detecting defect 820, the size of which may be characterized by a circle of at least a specified minimum diameter.

Coverage may be considered sufficient, for example, when paths can be generated to detect defects equal or greater than a selected size. Thus, when new paths are generated to satisfy coverage sufficiency, the test may be whether any defect of at least a selected size is detectable with the new set of paths. A defect of at least a selected size may be considered detectable if it always intersects at least one pitch-catch path when located anywhere within the transducer array. Other criteria defining coverage may be selected, the above description being only exemplary, and is not intended to be limiting. For example, selected criteria may be dependent on the length of the new path as well as on the amplitude and/or time-of-arrival of pulse signals.

Figures 8A, 8B, 8C:
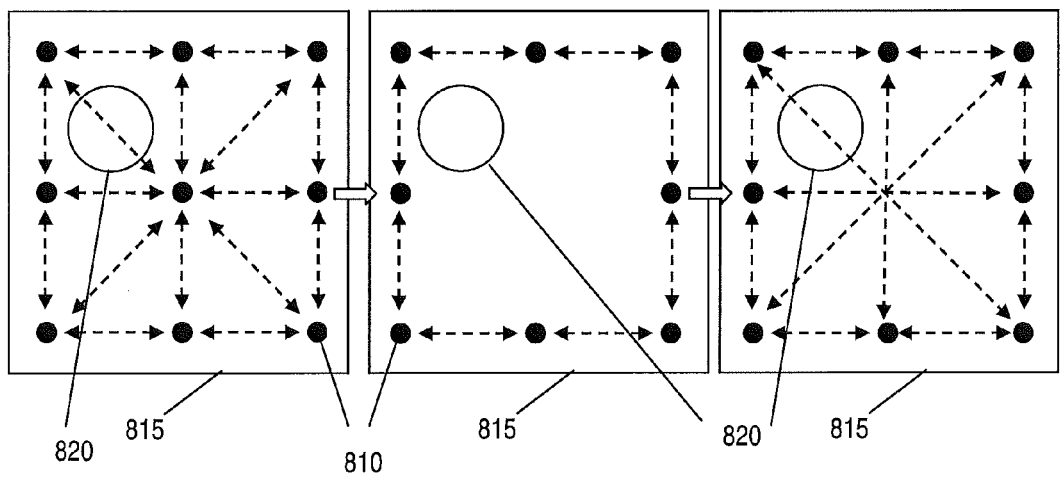
FIGS. 8 A-C illustrate self-healing in a transducer array by new-path generation, according to an embodiment of the present disclosure.

FIG. 8A represents array 815 with, for example, a generally square array of 9 transducers 810 in a 3×3 matrix. Defect 820 may be located in the top left quadrant of array 815. Paths between all adjacent vertical, horizontal or diagonal transducers 810 are indicated by broken double arrow lines. Defect 820 is clearly intersected, for example, by a path connecting the top left-most and center transducers 810.

FIG. 8B represents array 815 when center transducer 810 of array 815 is found, as a result of self-diagnosis method 400, missing, disbanded, or otherwise inoperative for structural health monitoring. Using method 600, all paths associated with defective (or missing) center transducer 810 are removed (block 640, FIG. 6). Defect 820 now occupies a region of the structure not covered by any of the remaining pitch-catch paths specified in the original configuration. Since coverage is now insufficient (according to block 650) to detect a defect 820 of at least the specified size, paths between other transducer pairs 810 may be added or extended to pass through the location of the missing transducer 810 or otherwise guarantee that defect 820 will be intersected by a path between two remaining transducers 810.

FIG. 8C represents array 815 with new paths added: diagonal paths between transducers 810 at opposite corners and horizontal and vertical paths between transducers 810 at the mid-points of the edges of array 815. Thus, in effect, all pitch-catch trajectories are recovered, and defect 820 now lies in at least one of the added paths, and may be detected. Accordingly, method 600 may continue (block 670) to verify self-diagnosis healing with pitch-catch signal transmission along the selected paths to determine if disbond defects, not found in impedance measurement method 400 still exist. When the predicted coverage is then obtained (i.e., when block 650 is satisfied with a YES result), testing of pitch-catch signals along the defined paths may be tested.

Figures 9A, 9B, 9C:
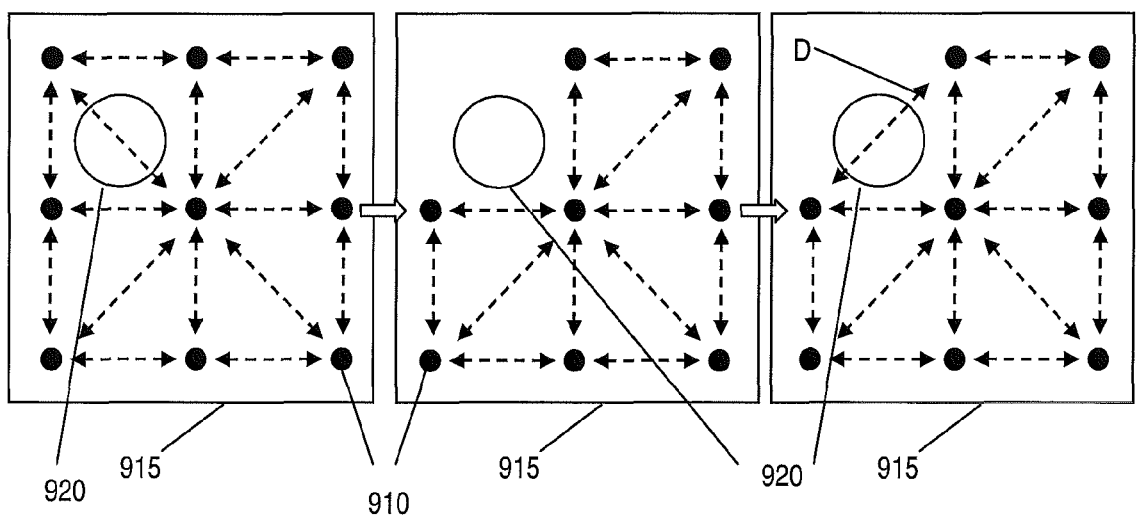
FIGS. 9 A-C illustrate self-healing in a transducer array by new-path generation, according to another embodiment of the present disclosure.

FIG. 9 illustrates an example of loss of a transducer 910 at a corner of an array 915, where the benefit of simply extending a path is not available. FIG. 9A is substantially identical to FIG. 8A. Defect 920 is located in substantially the same place and is of substantially the same size as defect 820. In FIG. 9B, the loss of the top left-most transducer results in the removal of three paths—one of which intersects defect 820 on a diagonal path with center transducer 910 of array 915. Method 600 may then add a new "alternate" diagonal path D that may intersect defects such as defect 920 located at the same position.

In cases where more than one transducer may be disbanded, where arrays of such transducers are typically arranged at least in two dimensions and/or consist of more than three transducers arranged in-line (i.e., collinearly), equivalent test scenarios may be implemented to verify each transducer for a disbond by using more complex (e.g., next-nearest neighbor in-line) paths.

Therefore, as illustrated in the above cases, testing path transmission between transducers and comparison to baseline data may enable detection of damaged or disbanded transducers 810 that are not apparent from simple pass/fail impedance measurements alone.

After the sensor array is "healed" in this manner, the remaining path data may then be passed on to a structural health monitoring reasoning process to determine if the structure itself is damaged, i.e., has detectable defects.

Having thus described embodiments of the present invention, persons of ordinary skill in the art will recognize that changes may be made in form and detail without departing from the scope of the invention. For example, arrays of transducers may be disposed in more than two dimensions, and arrays may be disposed in arrangements that are other than rectangular, square or other than regularly repeated patterns. Thus the invention is limited only by the following claims.

What is claimed is:

1. A method of performing self-diagnostics on an array of transducers, comprising:
    measuring an impedance of a selected one of the transducers to detect whether the selected one of the transducers is missing, or whether an electrical connection to the selected one of the transducers is damaged;
    generating pitch-catch signals along signal transmission paths between one or more pairs of the transducers;
    analyzing multiple ones of the pitch-catch signals between multiple pairs of the transducers according to selected criteria to determine whether one or more transducers of the pairs of the transducers are damaged, partially bonded, or fully unbonded;
    determining if one or more transducers of the pairs of the transducers are determined to be damaged, partially bonded, or fully unbonded:
        designating new signal transmission paths between the one or more pairs of the transducers to allow structural health monitoring of regions having the one or more damaged, partially bonded, or fully unbonded transducers; and
    if none of the transducers of the pairs of the transducers are determined to be damaged, partially bonded, or fully unbonded:
        designating no new signal transmission paths.

2. The method of claim 1, wherein measuring the impedance of the selected one of the transducers further comprises:
    applying a waveform voltage to the selected one of the transducers to measure the impedance;
    comparing the impedance to a reference value of impedance corresponding to a satisfactory transducer; and
    determining if the measured impedance indicates an open, short, or normal circuit connection to the transducer.

3. The method of claim 2, wherein comparing the impedance to the reference value further comprises determining a ratio of a first voltage signal to a second voltage signal, wherein the first voltage signal is measured across the selected one of the transducers in series with a reference resistor, and the second voltage signal is generated by a waveform generator.

4. The method of claim 1, wherein generating the pitch-catch signals along the signal transmission paths between the one or more pairs of the transducers further comprises:
    transmitting a signal from a first transducer to a second transducer and a third transducer, wherein the first, second, and third transducers are arranged in an inline sequential configuration; and
    detecting the signal at the second and third transducers.

5. The method of claim 1, wherein analyzing the multiple ones of the pitch-catch signals between the multiple pairs of the transducers according to the selected criteria further comprises:
    comparing the pitch-catch signals to the selected criteria, wherein the selected criteria includes baseline data of signals transmitted from a first baseline transducer to a second baseline transducer and a third baseline transducer, wherein the baseline data is obtained when the first, second, and third baseline transducers are arranged in an inline sequential configuration and determined to be properly functioning and properly bonded to a baseline structure; and
    determining, from the comparison of the pitch-catch signals to the selected criteria, if any of the transducers of the one or more pairs of the transducers is bonded, partially bonded, or fully unbonded.

6. The method of claim 5, wherein determining if any of the transducers of the one or more pairs of the transducers is damaged, partially bonded, or fully unbonded further comprises:
    identifying a fully unbonded or partially unbonded transducer from the one or more pairs of transducers.

* * * * *